US006286179B1

United States Patent
Byrne

(12) United States Patent
(10) Patent No.: US 6,286,179 B1
(45) Date of Patent: Sep. 11, 2001

(54) APPARATUS AND METHOD FOR REMOVING DEBRIS FROM THE LENS-CLEANING NOZZLE OF AN ENDOSCOPE

(76) Inventor: Donny M. Byrne, 9 Royal Dalton, Conroe, TX (US) 77304

( * ) Notice: Subject to any disclaimer, the term of this patent is extended or adjusted under 35 U.S.C. 154(b) by 0 days.

(21) Appl. No.: 09/411,573

(22) Filed: Oct. 4, 1999

Related U.S. Application Data

(60) Provisional application No. 60/104,760, filed on Oct. 19, 1998.

(51) Int. Cl.[7] ................................................. B08B 9/032
(52) U.S. Cl. ................. 15/304; 134/169 R; 134/169 C; 422/300
(58) Field of Search .................. 15/304, 344, 415.1; 134/169 R, 169 C; 422/292, 300

(56) References Cited

U.S. PATENT DOCUMENTS

| | | | |
|---|---|---|---|
| 3,044,475 | * | 7/1962 | Thompson ........................ 15/304 X |
| 3,175,590 | * | 3/1965 | Belknap ........................... 15/304 X |
| 4,660,249 | * | 4/1987 | Popovic ........................... 15/344 X |
| 4,733,428 | * | 3/1988 | Malinge et al. ................... 15/304 X |
| 5,555,601 | * | 9/1996 | Schultz ............................ 15/344 X |
| 6,041,794 | * | 3/2000 | Lin et al. ....................... 134/169 C X |

* cited by examiner

Primary Examiner—Philip R. Coe
(74) Attorney, Agent, or Firm—Harrison & Egbert

(57) ABSTRACT

A device for use in the cleaning of an endoscope having a body with a first end, a second end and a longitudinal passageway extending therebetween, a seal affixed to the body between the first and second ends, and a transverse passageway formed in the body between the second end and the seal. The transverse passageway communicates with the longitudinal passageway. The body has a central body portion of greater diameter than a remainder of the body. The seal is positioned between the central body portion and the transverse passageway. The first end is adapted for connection to a suction line. The body has a section with a diameter adapted to be received within an air/water cavity of the endoscope. A seal is affixed around the section so as to have a diameter suitable for sealing engagement with the valve cavity. A sealing shoulder is formed on the body between the transverse passageway and the second end so as to restrict air flow between the air/water inlet line to the air/water nozzle line.

10 Claims, 2 Drawing Sheets

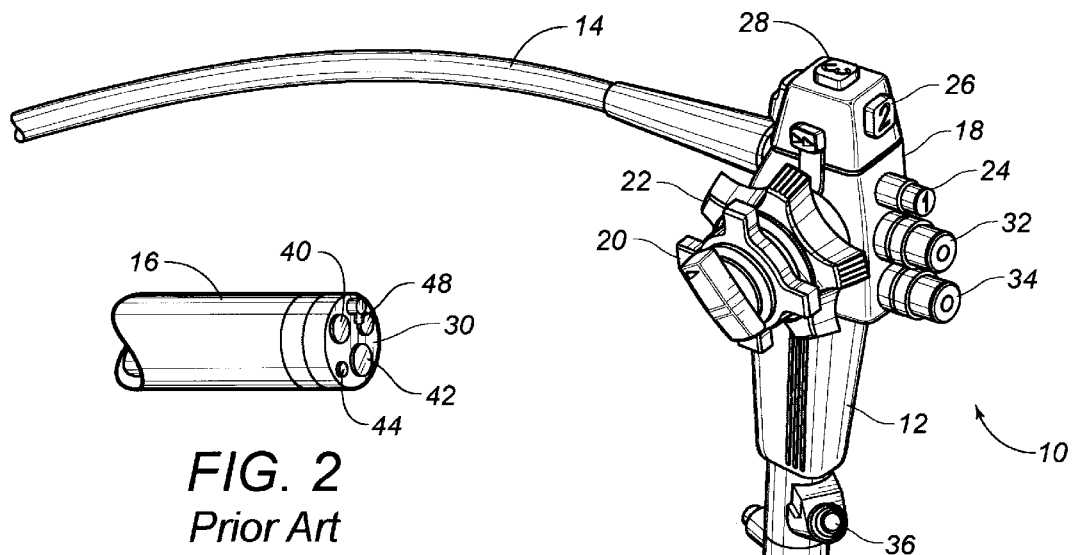
FIG. 2
*Prior Art*
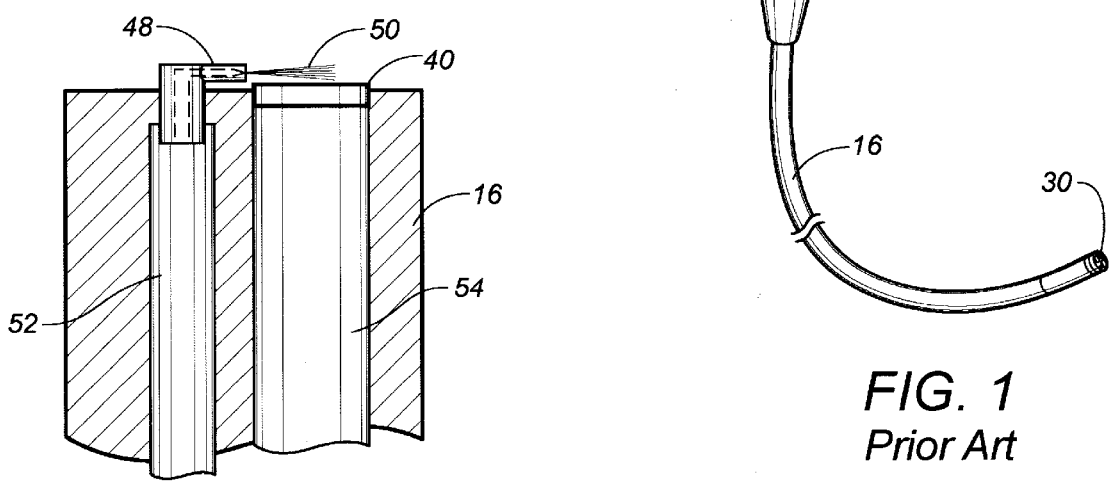
FIG. 1
*Prior Art*
FIG. 3
*Prior Art*
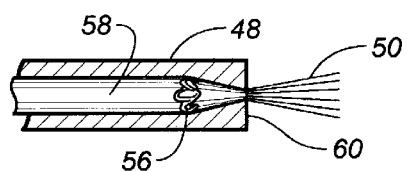
FIG. 4
*Prior Art*

APPARATUS AND METHOD FOR REMOVING DEBRIS FROM THE LENS-CLEANING NOZZLE OF AN ENDOSCOPE

RELATED APPLICATIONS

The present application is based upon prior filed Provisional Patent Application Ser. No. 60/104,760, filed on Oct. 19, 1998, and entitled "Apparatus and Method for Removing Debris from the Lens-Cleaning Nozzle of an Endoscope", presently pending.

TECHNICAL FIELD

The present invention relates to endoscopic systems. More particularly, the present invention relates to devices for cleaning the endoscopic system. Furthermore, the present invention relates to devices and methods for removing debris from the nozzle associated with the cleaning of the lens of the endoscopic system.

BACKGROUND ART

Endoscopic instruments have been developed to provide surgeons with an internal view of the organ or body passage requiring treatment. Such endoscopes typically have channels through which a miniaturized forceps, commonly called flexible instruments, are inserted and advanced. The endoscope assembly includes an elongated flexible cable equipped at one end with an eyepiece or other viewing means and at the other end with an optical head. Only the head is directly and externally connected to the instrument. The cable transmits images or image-producing signals from the illuminated operative site to the viewing means so that the surgeon will have visual confirmation of the action of the instrument's working end. A coherent optic bundle extends from the head and through the flexible cable through the eyepiece for providing the surgeon with visual confirmation of the instrument's tip or jaw action. The illuminating means may take the form a light-transmitting waveguide extending through the cable to illuminate the operative area. The waveguide is connected at its proximal end to a suitable high-intensity light source. The cable also provides a flow passage for the delivery of fluid (liquid or gas) for irrigation or other purposes. Typically, the flow passage and the illuminating means are disposed on opposite sides of the coherent image-transmitting waveguide.

In conventional practice, it is necessary to provide the optic head with a flow of sterile water. The passage of the sterile water across the optic head prevents the buildup of materials on the optic head. This flow of water operates, in a sense, like a windshield wiper/washer assembly.

In normal practice, the endoscopic instrument has a control body which is connected by a light guide tube to a light guide connector. The connector will include a plurality of connectors that can suitably receive various fittings. For example, the light guide connector can include a connector orifice that receives a grounding lug, a suction port, an air inlet, and a water inlet. As such, the air and water are delivered through the light guide connector, through the light guide tube and into the control body. Alternatively, the control body can also include a water port so as to allow water to be directly provided to the control body. Suitable valves are provided on the control body so as to control the flow of water through the control body and over the optic head of the instrument.

Referring to FIG. 1, there is shown an example of such an endoscopic system. The endoscopic system 10, in FIG. 1, shows an endoscope 12 into which an air/water inlet line 14 connects and from which an insertion tube 16 extends. The endoscope 12 has a control body 18 with a plurality of control members positioned thereon. A pair of control knobs 20 and 22 extend outwardly from one side of the control body 18. Remote control switches 24, 26 and 28 are positioned on the control body 18 so as to allow the surgeon to operate the distal end 30 of the insertion tube 16. A suction valve 32 is formed on the control body 18 which can be depressed so as to activate suction at the distal end 30. An air/water valve 34 is positioned below the suction valve 32 on the control body 18. The air/water valve 34 has a hole formed thereon. The surgeon can cover the hole with a finger for air sufflation. The valve 34 can be depressed so as to activate water feeding for the washing of the lens on the distal end 30. An instrument channel opening 36 is positioned adjacent to the control body 18 so as to allow for the insertion of forceps or other accessories into the insertion tube 16. The endoscope 12 allows the surgeon to carry out surgical activities within the human body while, simultaneously, viewing the action of such surgery through a lens formed on the distal end 30 of the insertion tube 16.

FIG. 2 is a detailed view of the distal end 30 of the insertion tube 16. As can be seen in FIG. 2, the distal end 30 has a lens 40 positioned for viewing outwardly of the distal end 30. An instrument channel 42 allows for forceps, and other accessories, to be extended outwardly of the distal end 30. A light guide 44 is provided on the distal end 30 so as to emit light outwardly of the distal end 30 so as to facilitate viewing through the objective lens 40. An auxiliary water nozzle 46 is also provided on distal end 30 so as to allow water feed in the same direction as the direction of viewing. Importantly, an air/water nozzle 48 is provided on the distal end 30 to feed water and air for the cleaning of the lens 40.

As can be seen in FIG. 3, the air/water nozzle 48 emits a stream 50 of air and water across the surface of the objective lens 40. The air and water are fed into the nozzle 48 through an air/water delivery tube 52. Air/water delivery tube 52 extends through the interior of the insertion tube 16. The air/water 50 is emitted from nozzle 48 so as to clean the outer surface of the objective lens 40 during use. In this manner, the nozzle 48 operates in the manner of a windshield washer/wipe assembly on an automobile. The nozzle 48 is important for the purpose of keeping debris, and other obstructions, from interfering with the view through the objective lens 40. A fiberoptic line 54 will extend to the objective lens 40 so as to allow the surgeon to view action on the interior of the human body.

FIG. 4 shows an example of what can occur when the nozzle 48 becomes obstructed with a piece of debris 56. In FIG. 4, it can be seen that the debris 56 is lodged in the wide portion of passageway 58 in nozzle 48. When the obstruction is lodged in this position, the spray 50 will be diminished or blocked. When this occurs, it is no longer possible to clean the objective lens 40. The obstruction 56 can occur on the interior of the passageway 58 for a variety of reasons. Accumulations of human debris around the objective lens 40 can wedge themselves in the area of the nozzle opening 60. Alternatively, the debris 56 can occur during the conventional cleaning of the endoscope 12. Even a small amount of blockage can result in the ineffective operation of the endoscopic system.

In conventional practice, whenever a sufficient amount of debris 56 resides in the area adjacent to the opening 60 of nozzle 48, it is necessary to send the endoscopic system 10 to a remote location for cleaning and repair. A very complicated proceeding is required so as to effectively remove the debris 56 from the nozzle 48 so as to allow the nozzle 48 to operate in a desired manner. When it is necessary to clean the endoscopic system 10, many costs can result. Initially, there is the repair cost for the endoscopic system. There is also the cost of shipping the unit to a suitable cleaning facility. Furthermore, there is a cost associated with the loss of use of the endoscopic system 10 by the hospital. Furthermore, there are costs associated with potential damage that can occur during shipping or repair. As such, a need has developed so as to allow the endoscopic system 10 to be suitably cleaned in the hospital environment at minimal costs.

It is an object of the present invention to provide an endoscopic cleaning system which effectively serves to remove debris from the air/water nozzle of the endoscopic instrument.

It is another object of the present invention to provide a method and apparatus for the cleaning of the air/water nozzle which can be carried out in a minimal amount of time and with a minimal amount of difficulty.

It is a further object of the present invention to provide a method and apparatus for the cleaning of the endoscopic instrument which eliminates the need for the shipment and downtime of the endoscopic instrument.

It is still a further object of the present invention to provide a method and apparatus for the cleaning of the air/water nozzle of an endoscopic instrument which is easy to use, relatively inexpensive, and easy to manufacture.

These and other objects and advantages of the present invention will become apparent from a reading of the attached specification and appended claims.

SUMMARY OF THE INVENTION

The present invention is a device for the cleaning of a nozzle of an endoscope. This device has a body with a size suitable for insertion into the air/water valve cavity of the endoscope body. The air/water valve cavity communicates with the air/water inlet line and communicates with the air/water nozzle line. The body can be used so as to be inserted in place of the air/water valve on the endoscope body.

The body of the present invention has a first end which extends outwardly of the endoscope body. The first end is suitable for attachment to a suction line. This first end of the body has a Christmas tree connection to as to allow it to be connected to a flexible tube associated with a suction device. A longitudinal passageway which extends through the body. This longitudinal passageway has one end opening at the first end and an opposite end opening at the second end of the body.

The second end of the body extends into the cavity. The second end of the body has the longitudinal passageway opening thereto. This opening of the longitudinal passageway will communicate with the air/water inlet line of the endoscope. As such, it allows the air feed into the endoscope to pass outwardly of the first end of the body and diverts such air passageway from entering the air/water nozzle line. A transverse passageway communicates with the longitudinal passageway and opens adjacent to the air/water nozzle line. A sealing shoulder is positioned on the body so as to contact a shoulder of the cavity between the air/water inlet line and the air/water nozzle line. In effect, the shoulder restricts air coming into the cavity from passing to the air/water nozzle line. As a result, the air/water nozzle line will only receive the suction from the suction line.

A seal is positioned on the body in the cavity above the air/water nozzle line in air-tight sealing relationship between the body and the wall of the cavity. The body of the present invention is formed of a polymeric material. The sealing device can be a O-ring elastomeric seal which fits tightly between the wall of the cavity and the exterior of the body.

The process of the present invention involves the steps of: (1) removing the air/water valve on the endoscope body; (2) inserting the cleaning body into the air/water valve cavity of the body; (3) attaching a suction line to one end of the cleaning body; (4) drawing a suction on the first end of the body so as to create a suction in the air/water nozzle line; and (5) pulling debris through the air/water nozzle line outwardly of the endoscope body through the suction line. After use and cleaning, the cleaning body can be removed from the air/water valve cavity and the air/water valve can be reinserted therein for reuse.

BRIEF DESCRIPTION OF THE DRAWINGS

FIG. 1 is a perspective view of an endoscopic instrument upon which the present invention can be used.

FIG. 2 is a detailed perspective view of the distal end of the insertion tube of the endoscopic system.

FIG. 3 is an interior view of the distal end of the insertion tube of an endoscopic instrument.

FIG. 4 is a detailed cross-sectional view illustrating the debris as lodged within the passageway of the air/water nozzle.

DETAILED DESCRIPTION OF THE PRESENT INVENTION

Figure 5:
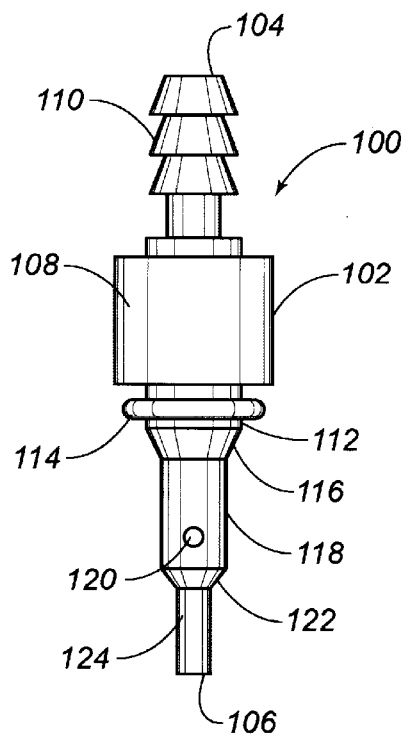
FIG. 5 is a side elevational view of the cleaning body of the present invention.

Referring to FIG. 5, there is shown at 100 the cleaning device as used in association with the present invention. The cleaning device 100 is suitable for use in place of the air/water valve associated with an endoscopic instrument. The device 100 includes a body 102 having a first end 104 and a second end 106. The body 102 has an area with a size suitable for insertion into the air/water valve cavity of the endoscope.

The first end 104 extends outwardly of a wide central body portion 108 of the body 102. The first end 104 has a Christmas tree connector 110 extending outwardly therefrom. A longitudinal passageway extends through the body 102 so as to have one end opening at first end 104. The Christmas tree connector 110 is suitable for connection to the interior of a flexible suction line. The central body portion 108 has a diameter greater than the diameter of the air/water valve cavity of the endoscope body.

The body 102 has a second end 106 which extends into the air/water valve cavity of the endoscope. A first section 112 extends downwardly from the central body portion 108. An elastomeric seal 114 is positioned around the first section 112. The seal 114 is an elastomeric O-ring seal suitable for establishing an air-tight sealing relationship between the wall of the cavity in the endoscope body and the exterior of first section 112. A tapered portion 116 extends downwardly into portion 118. First section 112 has a hole 120 formed therein. Another hole 120 (not shown) will emerge on the opposite side of first section 112. The positioning of holes 120 on opposite sides of the first section 112 allows the device 100 to be installed in any direction. Each of the holes 120 will communicate with the air/water valve cavity of the endoscope body so as to allow a suction to be drawn from the air/water nozzle line. A tapered shouldered area 122 extends downwardly from section 112 so as to connect with the second section 124. The end 106 is formed at the bottom of the second section 124. End 106 bears the opposite end of the longitudinal passageway. As such, the opening at end 106 will communicate with the air/water inlet line associated with the endoscopic system. The shoulder 122 will serve as a block between the longitudinal passageway opening at end 106 and the holes 120.

Figure 6:
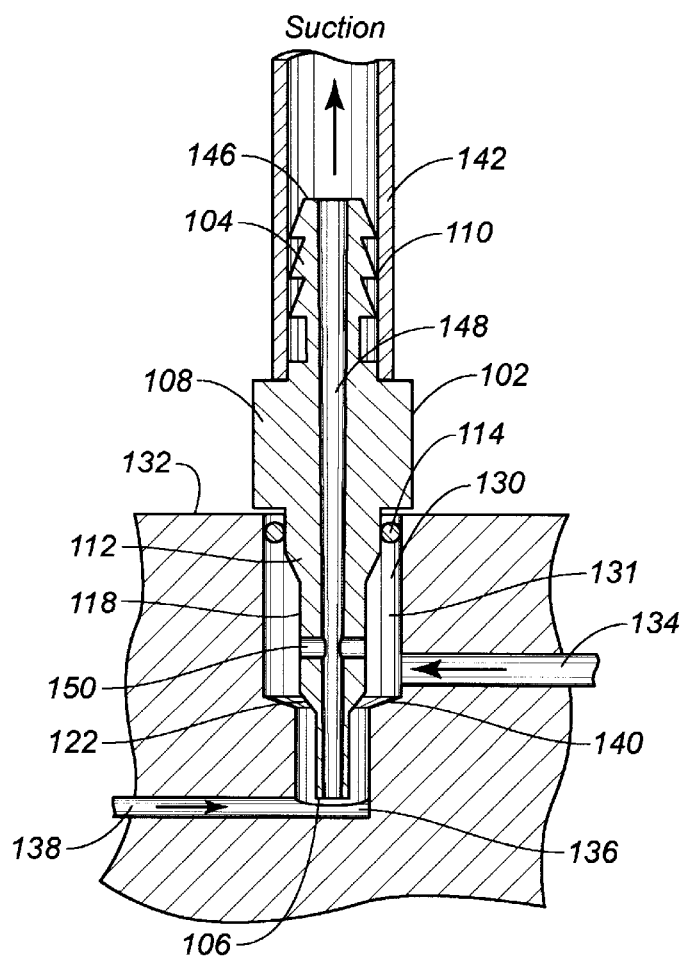
FIG. 6 is a cross-sectional view showing the cleaning body of the present invention as attached to the air/water valve cavity of an endoscopic body.

FIG. 6 shows the manner in which the body 102 is inserted into the cavity 130 of the endoscope body 132. In FIG. 6, it can be seen that the cavity 130 has a first interior area 131 which communicates with the air/water nozzle line 134. The cavity 130 shows a narrow area 136 which will communicate with the air/water inlet line 138. A shoulder 140 will extend between the first area 131 and the second area 136.

In FIG. 6, it can be seen that the first end 104 has a suction line 142 attached to the Christmas tree connector 110. As illustrated by the arrow in FIG. 6, a suction is drawn on the end 146 of the longitudinal passageway 148. As such, a suction device can be connected to the tube 142 so as to draw a suction on the longitudinal passageway 148. It can be seen that the longitudinal passageway 148 extends entirely through the body 102 so as to have one end emerging at end 104 and an opposite end emerging at end 106. The longitudinal passageway 148 has transverse passageway 150 opening to hole 120 and the hole on the opposite side of the first section 112 of the body 102.

In FIG. 6, it can be seen that the central body portion 108 has a surface which abuts the exterior of the endoscopic body 132. The seal 114 resides in interference-fit relationship with the wall of the cavity 130. As such, the seal 114 creates an air-tight seal at that location. The transverse passageway 150 allows suction to be drawn from the area 131 and from the air/water nozzle line 134. As such, the transverse passageway 150, in communication with the longitudinal passageway 148, serves to draw debris from the air/water nozzle line 138. Simultaneously, the shoulder 122 will block air flow from the air/water inlet line 138 into the air/water nozzle line 134. The opening of the longitudinal passageway 148 at the end 106 will allow the air from the air/water line 138 to pass through the longitudinal passageway 148.

Figure 7:
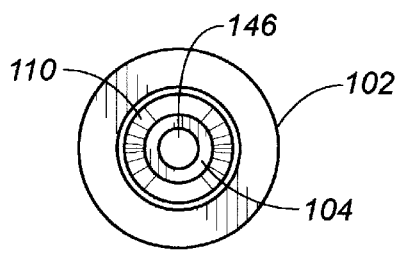
FIG. 7 is an end view of a first end of the cleaning body.

As can be seen in FIG. 7, the end 104 has opening 146 of the longitudinal passageway 148 emerging therefrom. The Christmas tree connector 110 extends outwardly from the end 104.

Figure 8:
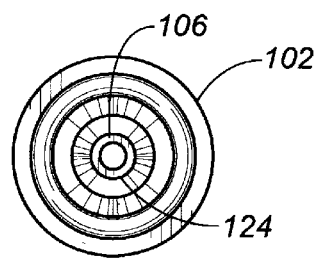
FIG. 8 is an opposite end view of the cleaning body of the present invention.

FIG. 8 shows the opposite end of the body 102. The longitudinal passageway 148 opens at end 106 of the bottom section 124 of the body 102.

In actual use, when an obstruction occurs in the air/water nozzle, the air/water valve 134 can be removed from its associated cavity. The device 100 of the present invention is inserted therein. A suction line can be connected to the Christmas-tree connector 110 so as to allow suction to be drawn through the air/water nozzle line. This suction will serve to pull the debris 56 from the nozzle 48 through the wide portion of the air/water nozzle line. As such, experiments have shown that the present invention allows such an obstruction to be easily drawn through the air/water nozzle line and, hence, free the nozzle 48 of such obstruction. If desired, the nozzle 48 can be placed into peroxide or an enzymatic cleaning solution. The peroxide will serve to break down any patient debris that may be lodged in the nozzle. As such, the present invention can be used so as to draw such air and cleaning solution through the nozzle so as to effectively clean the device. The present invention can also be used during the conventional cleaning of the endoscopic system 10. All that is necessary is simply draw sterile water through the nozzle as part of the cleaning procedure. As such, the present invention can eliminate the possibility of cleaning being the cause of the blockage of the nozzle. Once the debris has been effectively removed from the nozzle, the device 100 can be removed from the air/water valve cavity and the air/water valve inserted therefor. As a result, the present invention allows the nozzle to be effectively cleaned without the need for off-site cleaning procedures. The device 100 of the present invention can be easily manufactured, in an injection molding process, of a polymeric material. As a result, the device can be made so as to be disposable after use. The device can be manufactured in a relatively inexpensive manner.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. An apparatus comprising:

an endoscope having an air/water inlet line and an air/water nozzle line extending therefrom, said endoscope having a valve cavity communicating with said air/water inlet line and said air/water nozzle line; and a cleaning adapter removably received within said valve cavity, said cleaning adapter adapted to block air flow from said inlet line to said nozzle line and adapted to allow a suction to be applied to said nozzle line.

2. The apparatus of claim 1, said cleaning adapter comprising:

a body having a first end, a second end, and a longitudinal passageway extending through said body between said first and second ends;

a seal affixed to said body between said first and second ends; and a transverse passageway formed in said body between said second end and said seal, said tranverse passageway communicating with said longitudinal passageway.

3. The device of claim 2, said body having a central body portion of greater diameter than a diameter of said valve cavity, said seal interposed between a wall of said valve cavity and an exterior surface of said body.

4. The apparatus of claim 3, said body having a first section with a diameter less than said central body portion, said first section extending into said valve cavity, said transverse passageway extending through said first section so as to communicate with said nozzle line.

5. The apparatus of claim 4, said body having a second section extending from said first section to said second end, the cleaning adapter further comprising:

a sealing shoulder formed between said first section and said second section, said sealing shoulder positioned in said cavity so as to restrict air flow from said inlet line to said nozzle line.

6. The apparatus of claim 5, said second section having a smaller diameter than said first section.

7. The apparatus of claim 1, further comprising:
a suction line having an end detachably affixed to said first end of said body, said suction line adapted to supply a suction through said longitudinal passageway and through said transverse passageway so as to remove debris from said nozzle line.

8. The apparatus of claim 7, said first end having a Christmas tree fitting formed thereon.

9. The apparatus of claim 1, said cleaning adapter being formed of a polymeric material.

10. The apparatus of claim 1, said seal being an elastomeric O-ring seal in fluid-tight engagement with said cavity, said first end extending outwardly of said cavity.

* * * * *